United States Patent [19]

Freitas et al.

[11] Patent Number: 4,776,840
[45] Date of Patent: Oct. 11, 1988

[54] HAND-HELD MEDICAL EVACUATOR AND IRRIGATION DEVICE

[75] Inventors: Michael W. Freitas, Irving; Fred A. Allgood, Fort Worth, both of Tex.

[73] Assignee: Alteron, Inc., Hurst, Tex.

[21] Appl. No.: 101,723

[22] Filed: Sep. 28, 1987

[51] Int. Cl.⁴ .............................................. A61M 1/00
[52] U.S. Cl. ....................................... 604/33; 604/35; 604/38; 604/118; 604/119
[58] Field of Search ................................ 604/30–36, 604/39, 118, 119

[56] References Cited

U.S. PATENT DOCUMENTS

| | | | |
|---|---|---|---|
| 3,108,426 | 11/1963 | Noonan et al. | 604/33 |
| 3,749,090 | 7/1973 | Stewart | 604/33 |
| 4,668,215 | 5/1987 | Allgood | 604/30 |

Primary Examiner—Carroll B. Dority, Jr.
Attorney, Agent, or Firm—Roger N. Chauza

[57] ABSTRACT

A pistol-shaped frame (26) houses a fluid distribution assembly (58), including a plunger (46) operated by a trigger (30) for discharging fluid from a reservoir (60) through an outlet check valve (68). On return of the spring-loaded trigger (30), an inlet check valve (80) allows fluid to be drawn into the reservoir (60). A thumb-operated valve assembly (96) provides a fluid passage between an output (12) of the device and the outlet check valve (68) in one position, and in another position provides a vacuum passage between a vacuum inlet port (104) and the output (12). Trigger graduations (136) provide a visual indication of measured amounts of fluid dispensed by the device (10).

21 Claims, 1 Drawing Sheet

U.S. Patent                Oct. 11, 1988                4,776,840
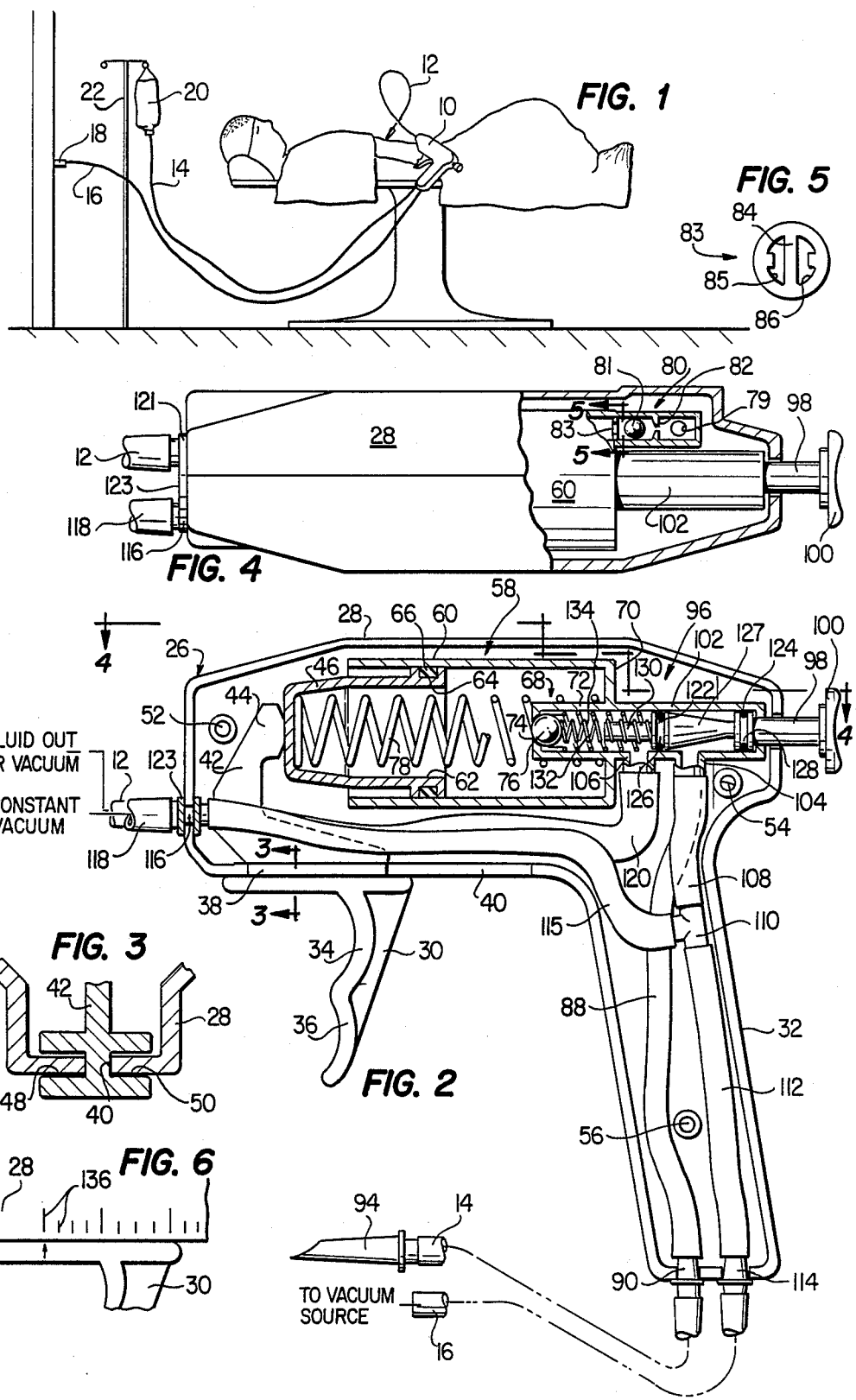

HAND-HELD MEDICAL EVACUATOR AND IRRIGATION DEVICE

TECHNICAL FIELD OF THE INVENTION

The present invention relates in general to medical instruments, and more particularly relates to equipment for selectively providing irrigation or vacuum facilities to a patient during surgery.

BACKGROUND OF THE INVENTION

Recent developments in surgical techniques have made possible the use of lasers for surgical operations. Particularly, lasers have been adapted to conduct surgery which is relatively noninvasive and thus results in less trauma to the patient. Lasers are also well adapted for microscopic surgery to repair or remove delicate organs.

The by-products or residue which results from laser surgery comprises smoke vapors and other gases generated by the laser beam cutting the tissue. Also, the laser beam causes small pieces of tissue to be removed from the area of surgery. These by-products which are generated during the surgical operation must be removed from the patient, otherwise the tissue and smoke vapors would interfere with the surgeon's ability to inspect the organ on which surgery is being conducted.

U.S. Pat. No. 4,668,215 discloses an irrigator-evacuator for assisting the surgeon or an assistant to selectively irrigate the area of surgery and to remove the residue using a remote vacuum source. Generally, a single flexible tube is extended to the area of surgery, and remotely controlled by the assistant. On command by the surgeon, the assistant can control the irrigator-evacuator by squeezing a rubber bulb aspirator for irrigating, and then actuating a valve to connect a vacuum source to the tube and extract both the residue and irrigation fluid. With such bulb, the irrigation of predetermined amounts of fluid for lavage purposes is difficult. The assistant can also maintain the valve actuated so that smoke or gas vapors can be evacuated from the area of operation during the laser surgery.

While the noted irrigator-evacuator provides a common device for selectively controlling the irrigation or evacuation around the area of operation, such device includes several inherent shortcomings. First, the device is not adapted for simultaneously providing an irrigation fluid and a source of vacuum to the operation area. Secondly, the liquid supply to the device requires pinching off to stop leakage or flow when the liquid source is either at the same height or elevated higher than the device. Additionally, the device of the noted patent is adapted for attachment to the bed sheet or gown of the patient, or to be held by one hand and operated by the other hand of the assistant.

From the foregoing, it can be seen that a need exists for improved medical irrigator/evacuator apparatus which is more readily adapted for holding in one hand, and for the single-handed operation thereof. An additional need exists for a hand-held medical device which can provide both an irrigation fluid and vacuum, if desired. An advantage of the invention is that it injects measured amounts of fluid to the area of operation.

SUMMARY OF THE INVENTION

In accordance with the present invention, the disclosed hand-held medical apparatus substantially reduces or eliminates the disadvantages and shortcomings associated with the corresponding prior art apparatus. According to the invention, there is disclosed a hand-held irrigation and evacuation device which is easily handled, can simultaneously provide a lavage and vacuum, can be operated by one hand and which can flood a body area or dispense measured amounts of fluid.

According to the preferred embodiment of the invention, the medical device is pistol-shaped, including a body section, a pistol-grip type of handle, and a spring-loaded trigger or lever. Housed by the body section is a fluid reservoir with a spring loaded plunger moveable by the trigger. The reservoir includes an inlet check valve connected by tubing exiting the handle of the device which, in turn, is connected to an intravenous (IV) or other liquid supply. The reservoir also includes an outlet check valve connected to a valve assembly for routing fluid through tubing out the front of the body section and to the patient. When the trigger is pulled, the plunger moves and the volume of the fluid reservoir is reduced, thereby forcing fluid out the outlet check valve and to the patient. When the trigger is released, the inlet check valve is opened, thereby drawing liquid from the external supply into the reservoir. The housing adjacent the trigger has index graduations which gauge the amount of fluid output to the patient.

Integral with the plunger-reservoir assembly is a valve assembly which includes a thumb-operated piston protruding from the rear end of the pistol body section. The valve assembly includes an inlet vacuum port connected to a source of vacuum, and an outlet port for carrying vacuum or liquid to the patient. The valve assembly is arranged to normally provide a passageway between the fluid reservoir and the outlet port, via the outlet check valve. When the piston of the valve assembly is depressed, the outlet port thereof is disconnected from the reservoir outlet check valve, and is connected to the inlet vacuum port. By depressing the thumb-operated piston, the vacuum source is connected through the valve assembly to the tube leading to the patient. The user of the irrigation/evacuation device of the invention can thus hold the device in one hand, and operate the trigger or the thumb-operated piston with the fingers of the same hand.

The valve assembly further includes a tapered shaft which is effective to meter the vacuum, depending on the amount by which the thumb-operated piston is depressed. The source of vacuum is also routed through the body of the device to a connector fixed to the frontal end of the pistol-shaped body. An additional connector provides a switched supply of irrigation fluid or vacuum. Thus, the surgeon's assistant can provide the surgical area with both a liquid for lavage purposes, and a vacuum to evacuate the area.

BRIEF DESCRIPTION OF THE DRAWINGS

Further features and advantages will become more apparent from the following and more particular description of the preferred embodiment of the invention, as illustrated in the accompanying drawings, in which like reference characters generally refer to the same parts or elements throughout the views, and in which:

FIG. 1 illustrates an environment in which the invention may be advantageously practiced;

FIG. 2. is a cross-sectional view of the hand-held irrigation/evacuation device of the invention;

FIG. 3 is a cross-section of the trigger, taken along Line 3—3 of FIG. 2;

FIG. 4 is a top view of the hand-held irrigation-/evacuation device, partially sectioned to illustrate the internal construction thereof;

FIG. 5 illustrates the webbed nature of the inlet check valve employed in the present invention; and FIG. 6 shows a portion of the irrigation/evacuation device, illustrating the graduation and reference marks for dispensing measured amounts of fluid.

DETAILED DESCRIPTION OF THE INVENTION

The hand-held irrigation/evacuation device of the invention may find a wide variety of medical applications, including laser surgery. The hand-held device 10 is shown in FIG. 1 as it would be employed in such an application. Extending as an output of the device is an irrigation/evacuation tube 12 which is manually located in the area of surgery by the surgeon's assistant. This advantageously allows the assistant to manipulate and control the device 10 with one hand, and use the other hand to properly place and maintain the irrigation-/evacuation tube 12 in a proper area adjacent the surgery. For the sake of simplicity, the laser surgical equipment is not shown, but is understood to be equipment which operates independently of the invention.

Provided as inputs to the hand-held device 10 is an irrigation liquid tube 14 and a vacuum tube 16. The vacuum tube 16 is terminated with a connector 18 and fastened to a source of vacuum which is conventionally available in hospital operating or recovery rooms. A vacuum on the order of 10-12 inches of mercury is adequate to provide a sufficient suction for evacuating smoke, vapors and irrigation fluids from the area of operation. Of course, for applications requiring long vacuum tubes 16, the vacuum may have to be increased.

The irrigation liquid tube 14 is shown connected to an intravenous fluid supply 20. The irrigation liquid tube 14 can be terminated in a trocar connection which is conventional for puncturing the IV supply 20 to obtain a sterile connection thereto. As noted, the IV supply 20 is shown elevated above the patient by a conventional stand 22. Importantly, when the irrigation fluid supply 20 is elevated above the hand-held device 10, the irrigation supply tube 14 need not be pinched off with a clamp to prevent the gravity flow of liquid through the device 10 to the outlet tube 12 thereof. As a result, the operation of the hand-held device 10 is independent of the elevation or position of the irrigation fluid supply 20. While the source of fluid 20 is shown as an IV container, the irrigation supply tube 14 can be connected to any source of fluid.

FIG. 2 illustrates in more detail the construction of the irrigation/evacuation device 10 of the invention. The hand-held irrigation/evacuation device 10 is constructed with a frame 26 which includes as major components thereof, a body section 28, a trigger 30 moveable with respect to the body section 28, and a handle 32. The body section 28 and handle 32 are constructed as an integral shell for housing the other essential components of the device 10. The frame 26 is constructed of an ABS type of plastic utilizing injection molding techniques. However, it is to be understood that other types of plastics or materials and fabrication techniques can be employed with equal advantage.

The trigger 30 includes finger-grip indentations 34 and 36 for gripping the same and pulling with the forefinger and middle finger of a user's hand. The trigger 30 includes a pair of channels, one shown as reference character 38, for slideable movement within a slot 40 or opening formed within the bottom of the body section 28. Formed integral with the trigger 30 is an arm 42 which is somewhat offset with respect to the grip part of the trigger 30. The arm 42 includes an end 44 which is adapted for pushing a cup-shaped plunger 46. While the trigger assembly of the invention is constructed for slideable movement, those skilled in the art may find that pivoting the trigger 30 about a point is also effective for ejecting fluid from the device 10.

With brief reference to FIG. 3, there is shown a cross-section through the trigger assembly for illustrating the construction thereof which allows slideable movement The body section 28 is formed in halves, and when put together, a slot 40 is formed. The trigger 30 has formed integral therewith a pair of opposing elongate channels 48 and 50 into which the slot edges of the body section 28 are captured when the halves of the body section 28 are assembled and fastened together. The tolerance between the channels 48 and 50 and the slot 40 are such that the trigger 30 does not bind and is easily slideable therein.

The halves of the molded frame are fastened together with screws at locations indicated by reference characters 52, 54 and 56.

With reference again to FIG. 2, there is illustrated the fluid distribution assembly 58 which includes the noted plunger 46 and a hollow barrel-shaped reservoir 60. The reservoir 60 has sidewalls formed of plastic, and is formed integral with one-half of the body section 28. The cup-shaped plunger 46 includes an opened end 62 with an external annular groove 64 formed therearound for receiving an elastomeric seal 66. The seal 66 is effective to provide a fluid seal between the plunger 46 and the inside surface of the reservoir 60. Hence, as the plunger 46 is forced into the reservoir 60 by the action of the trigger 30, the fluid therein is compressed and discharged through an outlet check valve 68. The outlet check valve 68 is formed in the end section 70 of the reservoir 60, opposite that in which the plunger 46 is disposed. The outlet check valve 68 is housed within a tubular plastic section 72 having a hole 74 in which a spring-loaded ball 76 is seated.

A coil spring 78 has one end thereof anchored around the outlet check valve housing 72, and the other end thereof which engages with the inside surface of the cup-shaped plunger 46 to force it to a position normally extending partially outside the reservoir 60. The spring 78 also functions to return the trigger 30, via the plunger 46, to the frontal end of the hand-held device 10. According to an important advantage of the invention, the coil spring 78 is effective to return the plunger 76 to its extended position and draw liquid into the reservoir. With this arrangement, the reservoir liquid is quickly replenished, and ready for dispensing when the trigger returns to its forward position.

Also formed integral with the reservoir 60 is an inlet check valve 80, shown in FIG. 4. The inlet check valve 80 is of the ball and seat type for allowing fluid to flow into the reservoir 60 when the spring 78 returns the plunger 46 to its extended position. The inlet check valve 80 has an inlet fitting 79 on its bottom side thereof for communicating fluid therethrough to the inlet check valve 80. The inlet fitting 79 is connected by a flexible plastic tubing 88 to an inlet connector 90 fixed within the bottom end of the frame handle 32. The inlet check valve 80 comprises a plastic ball 81 cooperating with a seat 82 on one side thereof, and a web network 83 on the reservoir side thereof. The seat 82 provides a seal with the ball to prevent fluid from draining or being discharged from the reservoir 60 back to the fluid source 20. The web network 83 is shown in detail in FIG. 5. The web network 83 includes a central web 84 and openings 85 and 86 for allowing fluid flow therethrough The irrigation/evacuation device 10 is thus operable to quickly and efficiently dispense a liquid, irrespective of the elevation of the liquid supply.

The inlet connector 90 may be of conventional construction for providing a friction fit to the tubing 88, as well as a friction fit to the flexible rubber tube 14 which is terminated with the trocar fitting 94. As noted above, the trocar fitting 94 is adapted for puncturing an IV container 20 allowing the fluid therefrom to be drawn into the hand-held irrigation/evacuation device 10 of the invention. Not shown for purposes of clarity are protrusions formed on the inside surface of the handle 32 which function to position and restrain the various flexible tubes routed therethrough.

Formed integral with the reservoir 60 is also a valve assembly 96 which is operable by a piston 98 that extends out of the back of the body section 28 The piston 98 includes an enlarged thumb piece 100 for pressing by a person's thumb to operate the valve assembly 96. The valve assembly 96 is enclosed within a tubular plastic section 102 which has a pair of spaced apart ports, defining an inlet vacuum port 104 and an outlet port 106. The inlet vacuum port 104 has fixed thereto a flexible tubing section 108 which is connected by a "T" 110 to another section of tubing 112. The tubing 112 is, in turn, connected to the other inlet connector 114 which serves to separately communicate a source of vacuum to the patient. An additional flexible tubing 115 extends from the "T" 110 to provide vacuum to an outlet connector 116 fixed within the frontal end of the irrigation/evacuation device 10. According to a feature of the invention, the outlet connector 116 can be fastened to a flexible tubing 118 which is also extended to the area of surgery of the patient to provide a constant source of vacuum to evacuate vapors or tissue material. Simultaneous supplies of an irrigation fluid and vacuum can thus be provided to the area of surgery. When not needed, the tubing 118 can be removed and the outlet connector 116 capped with a friction-fitting plastic cap (not shown).

The outlet port 106 of the valve assembly 96 is connected by a flexible tubing 120 to another outlet connector 121 (FIG. 4) fixed within the front end of the hand-held irrigation/evacuation device 10. The evacuation and irrigation tube 12 is connected to the noted outlet connector 121, and thereby to the outlet port 106 of the valve assembly 96. Both outlet connectors 116 and 121 are labeled as to "VAC only" for vacuum, and "H2O-VAC" for providing a constant vacuum and/or a switched liquid or vacuum. Such designations are formed within the frontal part of the body section 28 adjacent the connectors. The connectors 116 and 121 may be formed as an assembly on a plate 123 which has grooved edges for receiving therein the body section 28. As with the trigger 30, the body section 28 of the frame 26 includes an opening in the frontal part thereof such that when the halves of the frame 26 are assembled together, the connector plate 123 is captured and thus fixed to the frame 26.

The piston 98 of the valve assembly 96 includes a pair of spaced apart O-ring seals 122 and 124 formed in respective annular grooves 126 and 128 which are molded integral with the piston 98. The end of the piston 98 includes a stub shaft 130 which anchors one end of the outlet check valve spring 132. The spring 132 biases the ball 76 of the outlet check valve 68 so as to prevent irrigation fluid from draining out of the reservoir 60 in the absence of actuation of the trigger 30. This is especially important when the irrigation fluid supply 20 is elevated above the hand-held irrigation/evacuation device 10. An additional coil spring 134 encircles the check valve spring 132 and provides additional resistance to the depression of the thumb-operated piston 98. Indeed, as the thumb-operated piston 98 is depressed, the check valve spring 132 is also compressed, thereby offering additional resistance to the operation of the trigger 30, and thus the outlet check valve 68 is prevented from being operated. However, if sufficient force is applied to the finger grooves 34 and 36 of the trigger 30, the ball 76 can become unseated, thereby allowing fluid to be forced out of the reservoir 60 and into the outlet port 106. This assumes that the thumb-operated piston 98 is not depressed sufficiently such that the seal ring 122 blocks off the outlet port 106 from the outlet check valve 68.

According to another advantage of the invention, the piston 98 includes a tapered intermediate shaft 127 which is effective to meter the vacuum from the inlet port 104 to the outlet port 106. As can be seen, when the piston 98 is only depressed partially, the opening between the inlet port 104 and outlet port 106 is more constricted, than when the piston 98 is fully depressed. The tapered nature of the intermediate shaft 127 provides for a continuous metering of the vacuum to supply any desired amount of vacuum to the surgical area.

The valve assembly 96 is shown in FIG. 2 in its normal nondepressed position. As such, the O-ring seals 122 and 124 isolate a section of the valve assembly housing 102, thereby blocking the inlet port 104. On pulling the trigger 30, the cup-shaped plunger 46 reduces the volume of the reservoir 60 and forces the ball 76 of the outlet check valve 68 open, thereby forcing fluid through the outlet port 106 and to the irrigation/evacuation tube 12, via internal tubing 120. When the thumb-operated piston 98 is fully depressed, the O-ring seal 122 is moved past the left edge of the outlet port 106, thereby isolating the outlet check valve 68, and forming a fluid communication path between the inlet port 104 and the outlet port 106. Hence, the vacuum source is connected through the inlet and outlet ports 104 and 106 of the valve assembly 96 to the irrigation/evacuation tube 12. The O-ring seal 124 functions primarily to prevent the vacuum from escaping through the rear opening of the valve assembly case 102, through which the piston 98 protrudes.

In operation, the hand-held irrigation/evacuation device 10 can be employed to irrigate an area of surgery by simply grasping the handle 32 in the palm of the user's hand, and the trigger 30 with two fingers on the indented parts 34 and 36. A simple squeezing action is effective to move the trigger 30, and through the movement of the plunger 46, force irrigation fluids from the reservoir 60 through the outlet check valve 68 and to the irrigation/evacuation tube 12. For irrigating surgical areas with predefined amounts of fluids, the trigger 30 can be moved certain distances, according to the graduation marks 136, and thereby dispense predetermined volumes of fluid. This is highly important in many surgical operations where the total fluids input to the patient and given up by the patient are measured.

This feature of the invention is illustrated in FIG. 6. A reference mark 138 on the trigger can be visually gauged with the graduation marks on the body section 28 to determine the amount of fluid dispensed. Both sides of the device 10 can be marked with the graduation and reference marks to make the device 10 universally operable with right-handed or left-handed persons. In all other respects, the device 10 contrasts with the prior art device by being effectively and easily operated with either hand of the assistant.

When the trigger 30 is released, the spring 78 forces the cup-snaped plunger 46 outwardly, thereby closing the outlet check valve 68 and opening the inlet valve 80. Hence, fluid is automatically and quickly drawn into the reservoir 60 from the fluid supply 20. The recovery of liquid into the reservoir 60 is thus much faster than other irrigation devices heretofore available.

During the initial operation of the hand-held irrigation/evacuation device 10, the trigger 30 can be repeatedly pumped to thereby prime the device 10 to remove any air within the reservoir 60 and fill such reservoir 60 with irrigation fluids.

At any time in which it is desired to provide a full vacuum to the irrigation/evacuation tube 12, the thumb-operated piston 98 is simply fully depressed so that the vacuum source is connected via the inlet port 104 and outlet port 106 of the valve assembly 98 to the irrigation/evacuation tube 12. Otherwise, the thumb-operated piston 98 can be partially depressed to meter a desired amount of vacuum to the tube 12. Previously irrigated areas of the patient can thus be cleaned, whereupon any tissue residue and irrigation fluid is drawn through the tube 12 into the hand-held device 10 and toward the vacuum source. Any residue or smoke is collected in a container (not shown) located at the vacuum source for disposal or inspection of the body wastes.

From the foregoing, there is provided an irrigation and evacuation device which can be economically manufactured and efficiently utilized. The irrigation/evacuation device of the invention includes a check valve arrangement for preventing the inadvertent outflow of liquids from the device, thereby allowing the source of irrigation fluid to be elevated at any position with respect to the device. The construction and arrangement of the parts of the irrigation/evacuation device of the invention allows the device to be easily operated with one hand, and to discharge measured amounts of liquid or vacuum therefrom.

It is to be understood that the arrangements described herein are merely illustrative applications of the principles of the invention and that numerous other arrangements may be devised by those skilled in the art without departing from the spirit and scope of the invention, as defined by the appended claims.

What is claimed is:

1. A hand-held medical device for selectively supplying a liquid or a vacuum to a patient, comprising:
    a pistol-shaped frame having a body and a handle, and a moveable trigger, and including an outlet and a fluid inlet port and a vacuum inlet port;
    a plunger-reservoir assembly housed by said body, said plunger being responsive to trigger movements in one direction for drawing fluid through said inlet fluid port for storage within said reservoir, and responsive to trigger movements in another direction for forcing stored fluid from said reservoir through said outlet to the patient; and
    a valve assembly having a thumb-push means protruding from the rear of said body, said valve assembly providing a normally opened fluid passage between said reservoir and said outlet, and responsive to movement of said thumb-push means for closing said fluid passage and for coupling said vacuum inlet port to said outlet to the patient, whereby said medical device can be easily actuated with one hand.

2. The medical device of claim 1, wherein said frame is constructed in halves, and said plunger-reservoir assembly and said valve assembly are assembled integral with one said frame half.

3. The medical device of claim 2, wherein said plunger-reservoir assembly and said valve assembly are constructed integral with each other.

4. The medical device of claim 3, wherein said plunger-reservoir includes at one end thereof a trigger operated plunger operable with a reservoir for changing the volume thereof, and includes at an opposing end thereof an inlet check valve for drawing fluid into said reservoir, and an outlet check valve comprising a part of said valve assembly for discharging fluid from said reservoir.

5. The medical device of claim 1, wherein said valve assembly includes means for metering a vacuum from said vacuum inlet port to said outlet.

6. The medical device of claim 5, wherein said metering means includes a tapered shaft moveable with said thumb-push means for constricting the flow of said vacuum through an opening.

7. The medical device of claim 1, further including means for routing a supply of vacuum from said vacuum inlet port to an output of said medical device to provide a constant supply of vacuum to the patient.

8. Medical apparatus for use in selectively supplying a vacuum or a liquid to a patient, comprising:
    a pistol-shaped frame having a handle, a body section and a moveable trigger;
    a fluid distribution assembly housed by said body section, said valve assembly including a fluid reservoir and a plunger moveable with said trigger for applying a pressure to fluid within said reservoir, a first and second check valve for providing one-way passage of fluid respectively in and out of said reservoir, one said check valve being connected to a source of fluid, and the other said check valve being connected to a switching valve assembly; and
    said switching valve assembly including an inlet vacuum port normally disconnected from an outlet fluid port, said outlet fluid port being normally connected to said second check valve of said fluid reservoir, a push valve extending out of the rear of said body section and responsive to a manual pressure for disconnecting said second check valve from said outlet fluid port and for connecting said inlet vacuum port to said outlet fluid port.

9. The medical apparatus of claim 8, further including inlet connector means in said handle for connection thereto of a vacuum line and a fluid line for communicating vacuum and fluids respectively to said inlet vacuum port and said first check valve.

10. The medical apparatus of claim 8, further including a pair of outlet connectors fixed to the front end of said body section, one said outlet connection being connected to said outlet fluid port and the other said outlet connection being connected to a constant source of vacuum.

11. The medical apparatus of claim 8, wherein said reservoir comprises a barrel section and a plunger moveable with respect to said barrel section so as to change the valve within said barrel section.

12. The medical apparatus of claim 11, wherein said plunger is spring-biased so as to move in a direction for increasing the volume of said reservoir.

13. The medical apparatus of claim 12, wherein said second check valve protrudes inside said barrel at an end thereof which is opposite said plunger, and further including a coil spring positioned around said second check valve and engageable with said plunger.

14. The medical apparatus of claim 9, wherein said plunger is cup-shaped for receiving therein said coil spring.

15. The medical apparatus of claim 11, further including means for sealing said plunger to said barrel section.

16. The medical apparatus of claim 14, wherein said plunger is adapted for inward movement in contact with a backside of said reservoir, and said second check valve is disposed on said reservoir backside so that said check valve is disposed within said cup-shaped plunger when said plunger is fully moved within said barrel section.

17. The medical apparatus of claim 8, wherein said body section includes a track for slideable engagement with said trigger so that said trigger is longitudinally slideable for moving said plunger in a longitudinal path.

18. The medical apparatus of claim 17, wherein said trigger includes an arm extending into said body section for engaging said plunger, said arm being offset with respect to said trigger.

19. The medical apparatus of claim 17, wherein said trigger travel is limited by end stops which function to provide travel end points to said plunger.

20. The medical apparatus of claim 8, further including means for moving said trigger to predefined locations so as to dispense predefined volumes of liquids from said reservoir.

21. A hand-held medical irrigation/evacuation device, comprising:
 a frame having a body section integral with a handle;
 a trigger moveably fixed to said body section;
 a plunger-reservoir assembly fixed to said body section, said plunger being spring-biased in one direction, and responsive to movement of said trigger in the other direction for reducing the volume of said reservoir, said plunger being sealed to said reservoir to provide a fluid sealed chamber of varying volume;
 an inlet check valve for allowing fluid flow into said reservoir in response to movements of said plunger by said spring;
 an outlet check valve for allowing discharge of fluid from said reservoir in response to movement of said plunger by said trigger;
 a piston-operated valve assembly comprising an inlet port and an outlet port, said valve assembly having means for connecting said reservoir to said outlet port via said outlet check valve when in a first position, and for connecting said inlet port to said outlet port when in a second position;
 tube means for connecting said inlet port to a source of vacuum;
 tube means for connecting said outlet port to a tube directed to said patient; and
 tube means for connecting said inlet check valve to a fluid source.

* * * * *

UNITED STATES PATENT AND TRADEMARK OFFICE
CERTIFICATE OF CORRECTION

PATENT NO.   :   4,776,840
DATED        :   Oct. 11, 1988
INVENTOR(S)  :   Freitas et al.

It is certified that error appears in the above-identified patent and that said Letters Patent is hereby corrected as shown below:

Column 5, line 6, after therethrough, add --.--.

Column 5, line 23, after section 28, add--.--.

Column 7, line 12, change "snaped" to --shaped--.

Signed and Sealed this

Twentieth Day of June, 1989

Attest:

DONALD J. QUIGG

*Attesting Officer*   Commissioner of Patents and Trademarks